US010166169B2

(12) United States Patent
Illindala

(10) Patent No.: US 10,166,169 B2
(45) **Date of Patent: *Jan. 1, 2019**

(54) CHEST COMPRESSION DEVICE

(71) Applicant: ZOLL Circulation, Inc., San Jose, CA (US)

(72) Inventor: Uday Kiran V. Illindala, San Jose, CA (US)

(73) Assignee: ZOLL Circulation, Inc., San Jose, CA (US)

( * ) Notice: Subject to any disclaimer, the term of this patent is extended or adjusted under 35 U.S.C. 154(b) by 216 days.

This patent is subject to a terminal disclaimer.

(21) Appl. No.: 15/137,875

(22) Filed: Apr. 25, 2016

(65) Prior Publication Data

US 2016/0310359 A1 Oct. 27, 2016

Related U.S. Application Data

(63) Continuation of application No. 14/042,382, filed on Sep. 30, 2013, now Pat. No. 9,320,678.

(51) Int. Cl.
*A61M 11/00* (2006.01)
*A61H 31/00* (2006.01)

(52) U.S. Cl.
CPC ... *A61H 31/006* (2013.01); *A61H 2201/1207* (2013.01); *A61H 2201/1215* (2013.01); *A61H 2201/1664* (2013.01); *A61H 2201/5043* (2013.01)

(58) Field of Classification Search
CPC ....... A61H 31/00; A61H 2031/001–2031/008; A61H 2201/0157; A61H 2201/0161; A61H 2201/12; A61H 2201/1215; A61H 2201/123; A61H 2201/1481; A61H 2201/149; A61H 2201/1207; A61H 2201/5043
USPC ...... 601/41–44, 107, 108, 151, 152; 600/21, 600/22; 128/870
See application file for complete search history.

(56) References Cited

U.S. PATENT DOCUMENTS 3,425,409 A 2/1969 Isaacson et al.
3,739,771 A 6/1973 Gaquer et al.
5,634,886 A 6/1997 Bennett
(Continued)

FOREIGN PATENT DOCUMENTS

WO WO2012156994 11/2012

OTHER PUBLICATIONS

Extended European Search Report dated Mar. 31, 2017 from European Patent Application No. 14847305.1.

*Primary Examiner* — Steven Douglas
(74) *Attorney, Agent, or Firm* — K. David Crockett, Esq.; Paul J. Backofen, Esq.; Crockett & Crockett, PC

(57) ABSTRACT

A chest compression device includes a piston to apply compression to the sternum and incorporates leaf springs simultaneously driven by the piston to apply lateral compression to the thorax during chest compressions. A motor in the chest compression device provides motive power to cyclically extend and contract the piston to provide therapeutic chest compressions. One end of each leaf spring is operably connected to the piston and the other end of each leaf spring is secured to the backboard/base or to a support leg of the chest compression device such that during extension of the piston, each leaf spring is compressed against the device base or leg which causes the springs to flex and provide lateral compression of the patient's thorax in addition to the sternal compression of the piston.

8 Claims, 5 Drawing Sheets

(56) References Cited

U.S. PATENT DOCUMENTS

| | | | |
|---|---|---|---|
| 6,066,106 | A | 5/2000 | Sherman et al. |
| 6,142,962 | A | 11/2000 | Mollenauer et al. |
| 6,398,745 | B1 | 6/2002 | Sherman et al. |
| 6,616,620 | B2 | 9/2003 | Sherman et al. |
| 6,648,841 | B1 | 11/2003 | Sessler |
| 7,226,427 | B2 | 6/2007 | Steen |
| 7,347,832 | B2 | 3/2008 | Jensen et al. |
| 7,354,407 | B2 | 4/2008 | Quintana et al. |
| 7,410,470 | B2 | 8/2008 | Escudero et al. |
| 7,569,021 | B2 | 8/2009 | Sebelius et al. |
| 7,841,996 | B2 | 11/2010 | Sebelius et al. |
| 8,690,804 | B2 | 4/2014 | Nilsson et al. |
| 8,753,298 | B2 | 6/2014 | Sebelius et al. |
| 8,888,725 | B2 | 11/2014 | Parascandola et al. |
| 9,107,800 | B2 | 8/2015 | Sebelius et al. |
| 2003/0181834 | A1 | 9/2003 | Sebelius et al. |
| 2004/0116840 | A1 | 6/2004 | Cantrell et al. |
| 2006/0229535 | A1 | 10/2006 | Halperin |
| 2007/0276298 | A1 | 11/2007 | Sebelius et al. |
| 2009/0260637 | A1 | 10/2009 | Sebelius et al. |
| 2010/0004571 | A1 | 1/2010 | Nilsson et al. |
| 2010/0004572 | A1 | 1/2010 | King |
| 2010/0063425 | A1 | 3/2010 | King et al. |
| 2010/0185127 | A1 | 7/2010 | Nilsson et al. |
| 2011/0308534 | A1 | 12/2011 | Sebelius et al. |
| 2011/0319797 | A1 | 12/2011 | Sebelius et al. |
| 2012/0226205 | A1 | 9/2012 | Sebelius et al. |
| 2012/0283608 | A1 | 11/2012 | Nilsson et al. |
| 2014/0121576 | A1 | 5/2014 | Nilsson et al. |
| 2014/0180180 | A1 | 6/2014 | Nilsson et al. |
| 2014/0207031 | A1 | 7/2014 | Sebelius et al. |
| 2014/0303530 | A1 | 10/2014 | Nilsson et al. |

CHEST COMPRESSION DEVICE

RELATED APPLICATIONS

This application is a continuation of U.S. patent application Ser. No. 14/042,382 filed (Sep. 30, 2013) now U.S. Pat. No. 9,320,678.

FIELD OF THE INVENTIONS

The inventions described below relate to the field of cardiopulmonary resuscitation (CPR) chest compression devices.

BACKGROUND OF THE INVENTIONS

Cardiopulmonary resuscitation (CPR) is a well-known and valuable method of first aid used to resuscitate people who have suffered from cardiac arrest. CPR requires repetitive chest compressions to squeeze the heart and the thoracic cavity to pump blood through the body. Artificial respiration, such as mouth-to-mouth breathing or bag mask respiration, is used to supply air to the lungs. When a first aid provider performs manual chest compression effectively, blood flow in the body is about 25% to 30% of normal blood flow.

In efforts to provide better blood flow and increase the effectiveness of bystander resuscitation efforts, various mechanical devices have been proposed for performing CPR. Among the variations are pneumatic vests, hydraulic and electric piston devices as well as manual and automatic belt drive chest compression devices.

Piston-based chest compression systems are illustrated in Nilsson, et al., *CPR Device and Method*, U.S. Patent Publication 2010/0185127 (Jul. 22, 2010), Sebelius, et al., *Support Structure*, U.S. Patent Publication 2009/0260637 (Oct. 22, 2009), Sebelius, et al., *Rigid Support Structure on Two Legs for CPR*, U.S. Pat. No. 7,569,021 (Aug. 4, 2009), Steen, *Systems and Procedures for Treating Cardiac Arrest*, U.S. Pat. No. 7,226,427 (Jun. 5, 2007) and King, *Gas-Driven Chest Compression Device*, U.S. Patent Publication 2010/0004572 (Jan. 7, 2010) all of which are hereby incorporated by reference.

Our own patents, Mollenauer et al., *Resuscitation device having a motor driven belt to constrict/compress the chest*, U.S. Pat. No. 6,142,962 (Nov. 7, 2000); Sherman, et al., *CPR Assist Device with Pressure Bladder Feedback*, U.S. Pat. No. 6,616,620 (Sep. 9, 2003); Sherman et al., *Modular CPR assist device*, U.S. Pat. No. 6,066,106 (May 23, 2000); and Sherman et al., *Modular CPR assist device*, U.S. Pat. No. 6,398,745 (Jun. 4, 2002), and Escudero, et al., *Compression Belt System for Use with Chest Compression Devices*, U.S. Pat. No. 7,410,470 (Aug. 12, 2008), show chest compression devices that compress a patient's chest with a belt. Our commercial device, sold under the trademark AUTOPULSE®, is described in some detail in our prior patents, including Jensen, *Lightweight Electro-Mechanical Chest Compression Device*, U.S. Pat. No. 7,347,832 (Mar. 25, 2008) and Quintana, et al., *Methods and Devices for Attaching a Belt Cartridge to a Chest Compression Device*, U.S. Pat. No. 7,354,407 (Apr. 8, 2008).

As mechanical compressions are performed by piston-based chest compression systems, the patient's rib cage hinges or shifts about the sternum resulting in lateral spreading of the thorax and the effectiveness of the automated chest compressions are diminished. The repeated extension and retraction of the piston often results in the piston and compression cup moving or "walking" up the patient's chest toward the neck or moving down toward the patient's abdomen.

SUMMARY

The devices and methods described below provide for a chest compression device using a piston to apply compression to the sternum and incorporating leaf springs simultaneously driven by the piston to apply lateral compression to the thorax during chest compressions. A motor in the chest compression device provides motive power to cyclically extend and contract the piston to provide therapeutic chest compressions. One end of each leaf spring is operably connected to the piston and the other end of each leaf spring is secured to the backboard/base or to a support leg of the chest compression device such that during extension of the piston, each leaf spring is compressed against the device base or leg which causes the springs to flex and provide lateral compression of the patient's thorax in addition to the sternal compression of the piston.

DETAILED DESCRIPTION OF THE INVENTIONS

Figure 1:
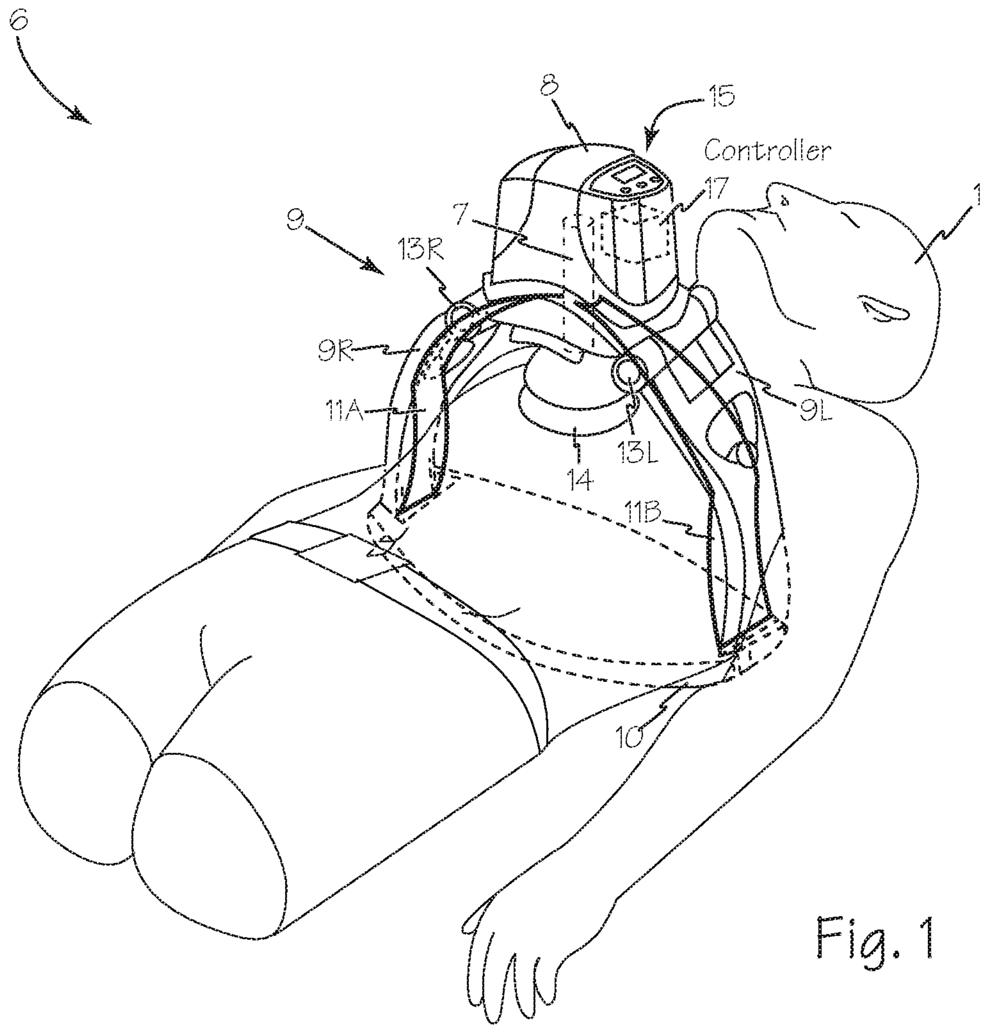
FIG. 1 is a perspective view of the chest compression device engaging a patient.

FIG. 1 illustrates the chest compression device fitted on a patient 1. The chest compression device 6 applies compressions with the piston 7. The piston is disposed within compression unit 8 which is supported over the patient with a frame or gantry 9 having two legs 9L and 9R fixed to a backboard 10. Compression unit 8 is connected to legs 9L and 9R at hinges 13R and 13L. Leaf springs 11A and 11B are operably connected between piston 7 and either backboard 10 or to support legs 9L and 9R through hinges 13R and 13L. Springs 11A and 11B may be formed of a single layer of material or they may be formed of two or more layers or two or more parallel springs.

Figure 2:
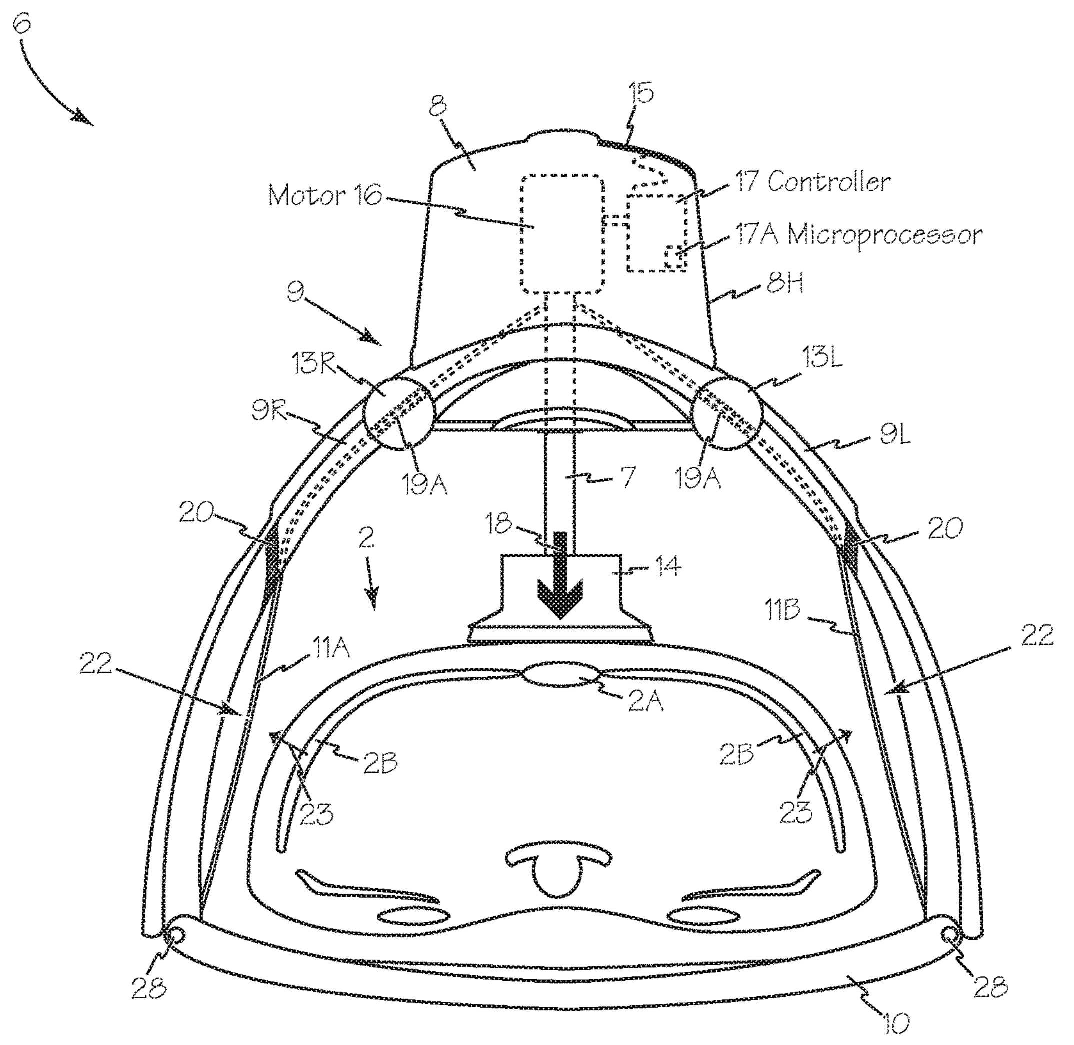
FIG. 2 is an end view of the chest compression device ready to commence compressions.

When disposed about the patient, the frame extends over thorax 2 of the patient so that the piston is disposed apposing sternum 2A to contact the patient's chest directly over the sternum, to impart compressive force on the sternum of the patient as shown in FIG. 2. Piston 7 may include a removable compression pad 14 adapted to contact the patient's chest. The chest compression device is controlled using controller 17 which is operated by a rescuer through interface 15, which includes a display to provide instructions and prompts to a rescuer and includes an input device to accept operating instructions from the rescuer.

As illustrated in FIG. 2, compression unit 8 is enclosed by housing 8H. Piston 7 is driven, either directly or indirectly, by motor 16 under control of controller 17 to extend and retract piston 7. Controller 17 may include one or more microprocessors such as microprocessor 17A. Cyclic extension and retraction of piston 7 causes cyclic exertion of compressive force 18 to patient's sternum 2A. Controller 17 actuates and controls operation of motor 16 and other elements or components of chest compression device 6. Controller 17 may include one or more sets of instructions, procedures or algorithms to control actuation and operation of the motor and other elements or components of device 6. Piston based chest compression devices often include one or more coiled springs around the piston to speed the retraction of the piston during the decompression phases of the chest compression-decompression cycles. Inclusion of springs 11A and 11B provide sufficient upward force to obviate the need for coiled springs for decompression.

Springs 11A and 11B are connected between piston 7 and legs 9L and 9R and the springs pass through a slot or other opening in hinges 13R and 13L such as slots 19A and 19B. Passage of the springs through slots 19A and 19B prevents the upper portions of the springs from flexing or bending during compression. Shoulders or other frictional elements such as shoulders 20 may be provided on, or attached to legs 9L and 9R to engage the springs and redirect the compressive force applied to the top of the springs down to the distal end of the springs where they engage the backboard or the legs. The redirection of force permits the lower or distal portion of each spring, distal portions 22A and 22B respectively, to flex or bow to apply lateral force during chest compression. During application of a compressive force such as force 18 to a patient's sternum, ribs 2B move as if hinged about sternum 2A. There is a reactive movement of ribs 2B which results in rotation of the ribs and lateral movement 23 of the ribs as shown. The extension of piston 7 to apply compressive force to the patient's sternum causes springs 11A and 11B to slide through slots 19A and 19B respectively and engage shoulders 20 and flex and apply lateral resistive force to the patient's ribs.

Figure 3:
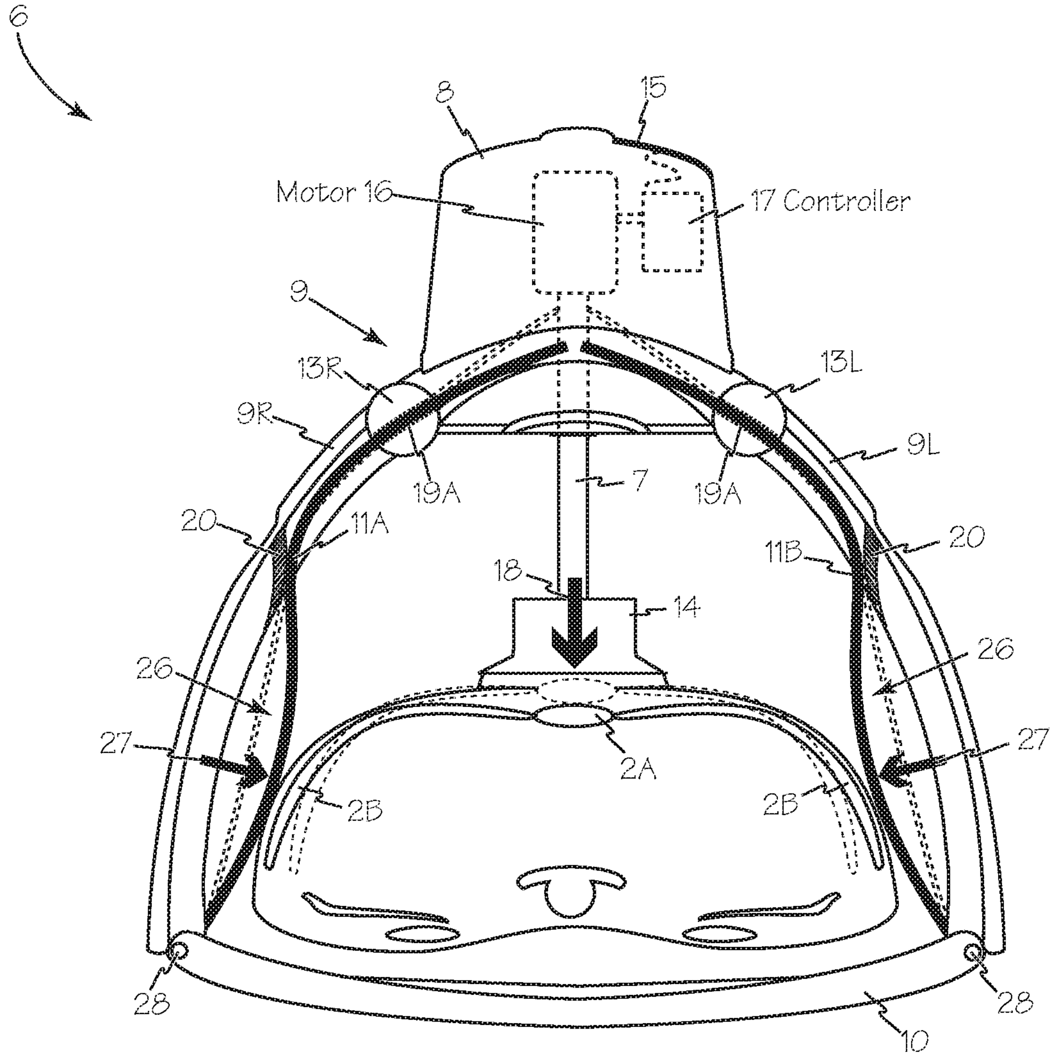
FIG. 3 is an end view of the chest compression device at full compression.

Referring now to FIG. 3, leaf springs 11A and 11B are connected between both piston 7 and legs 9L and 9R or backboard 10 such that extension of piston 7 causes leaf spring 11A and leaf spring 11B to form load bearing arch shape such as arch 26 to exert a lateral resistive force 27 against ribs 2B as illustrated.

To engage a patient in chest compression device 6 of FIG. 1, chest compression device 6 may be slid over patient 1 until the patient is oriented with piston 7 apposing sternum 2A. Alternatively, support legs 9L and 9R may be separated from backboard 10 at attachment points 28. Patient 1 is then oriented on backboard 10, support legs 9L and 9R are reengaged to backboard 10 with piston 7 apposing sternum 2A of patient 1. Chest compression device 6 may then be activated to provide chest compressions to patient 1.

Figure 4A:
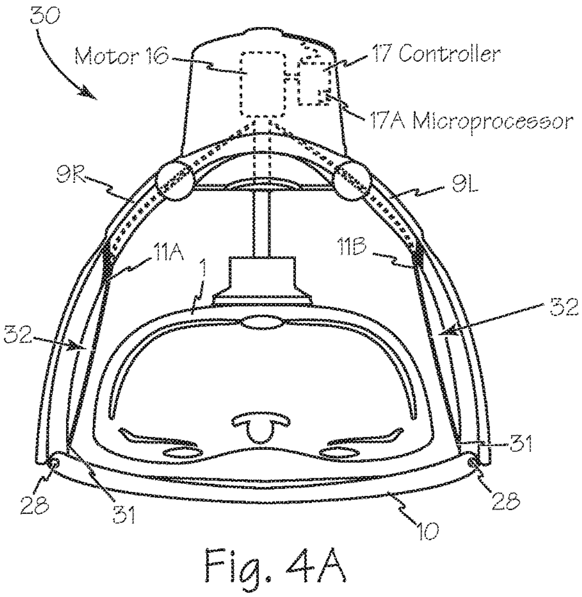
FIGS. 4A, 4B and 4C are end views of the chest compression device with adjustable springs ready to commence compressions.
Figure 4B:
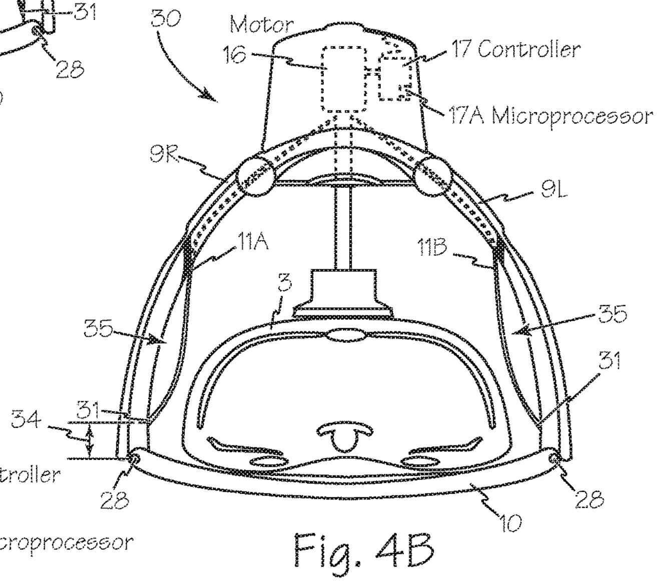
Figure 4C:
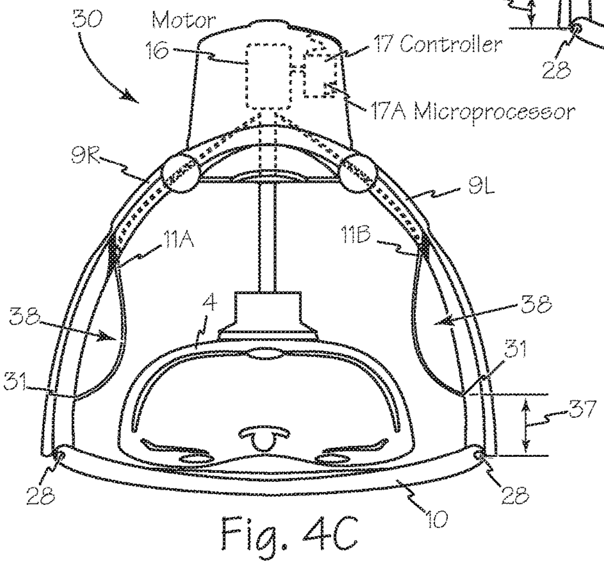

Referring now to FIGS. 4A, 4B and 4C, chest compression device 30 enables springs 11A and 11B to be preloaded to accommodate patients of different sizes. Patient 1 of FIG. 4A has a large chest, patient 3 of FIG. 4B has a medium size chest and patient 4 of FIG. 4C has a small chest. Springs 11A and 11B of FIG. 4A are adjusted for minimal preload and distal ends 31 of the springs engage legs 9L and 9R at or near attachment points 28. This configuration results in little or no preload of the springs and minimal load bearing arch 32 when the piston is fully retracted. With patient 3 of FIG. 4B, the distal ends 31 of the springs engages legs 9L and 9R a first distance 34 away from attachment points 28. This intermediate preload position results in first preload arch 35 which adds to the load bearing arch created by the compression of the springs to engage the medium size chest of patient 3 during chest compressions. With patient 4 of FIG. 4C, the distal ends 31 of the springs engages legs 9L and 9R a second distance 37 away from attachment points 28. This maximum preload position results in second preload arch 38 which adds to the load bearing arch created by the compression of the springs to engage the small size chest of patient 4 during chest compressions.

Figure 5:
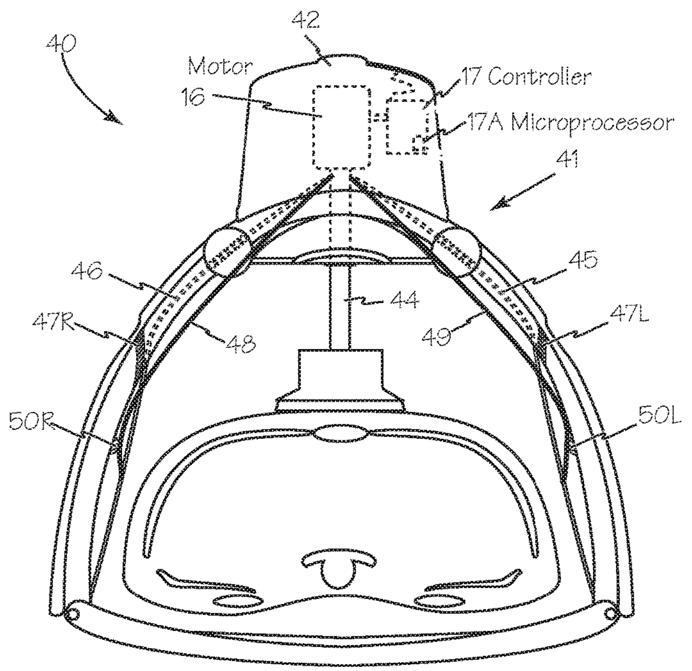
FIG. 5 is an end view of the chest compression device with dual springs ready to commence compressions.
Figure 6:
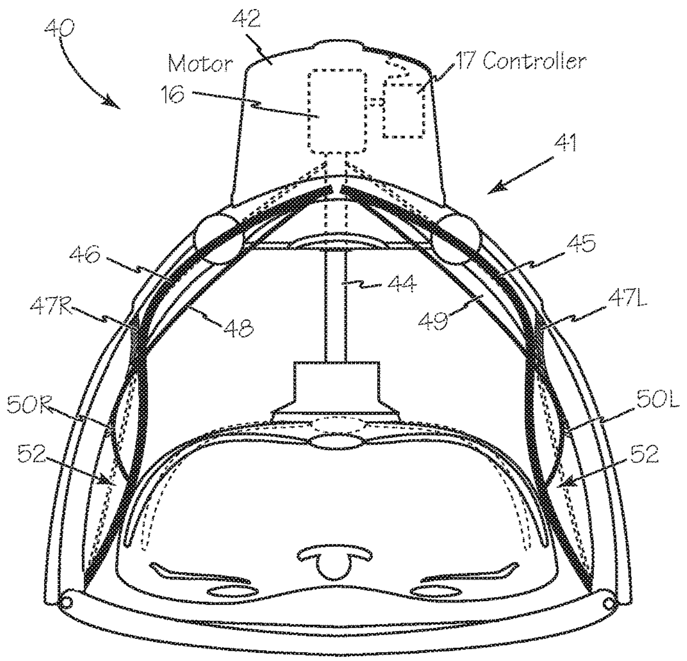
FIG. 6 is an end view of the chest compression device with dual springs at full compression.

Referring now to FIGS. 5 and 6, chest compression device 40 includes frame or gantry 41 supporting compression unit 42 and piston 44 to perform cyclic chest compressions. Primary springs 45 and 46 are oriented similar to springs 11A and 11B as discussed above. Primary springs 45 and 46 frictionally engage shoulders 47L and 47R respectively. Secondary springs 48 and 49 attach to piston 44 and frictionally engage secondary shoulders 50R and 50L respectively. Shoulders 51R and 50L are configured and oriented to enable secondary springs 48 and 49 to translate longitudinally and support and urge primary springs into a load bearing arch shape 52.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

I claim:

1. A device for performing cardiopulmonary resuscitation on a patient comprising:

a backboard;

a support frame having two legs secured to the backboard, the two legs supporting a compression unit apposing the backboard;

a motor enclosed within the compression unit;

a piston having a distal end and a proximal end, the proximal end of the piston operably coupled to the motor and the motor configured to extend the piston distally and withdraw the piston proximally relative to the compression unit, the compression unit secured to the support frame with the piston apposing the backboard;

two resilient members, each resilient member having a first end and a second end, the first end of each resilient member operably secured to the piston, the second end of each resilient member operably secured to one of the two legs, such that extension of the piston causes each resilient member to form an arch suitable to apply lateral force to the patient's chest.

2. The device of claim 1 further comprising:

a control unit operably connected to the motor and including a microprocessor to control the motor and the piston.

3. The device of claim 2 wherein the control unit is programmed using one or more sets of instructions to control actuation and operation of the motor.

4. The device of claim 2 further comprising:

a display operably connected to the control unit to enable activation and deactivation of the motor.

5. The device of claim 1 further comprising:

a compression pad removably engaging the distal end of the piston.

6. A method of performing cardiopulmonary resuscitation on a patient comprising the steps:

providing the device for performing cardiopulmonary resuscitation of claim 1;
orienting the patient on the backboard;
securing the support frame to the backboard with the piston apposing the patient's sternum; and
operating the chest compression device to cyclically compress the patient's chest with the piston and simultaneously apply lateral force to the patient's chest with the two resilient members.

7. A method of performing cardiopulmonary resuscitation on a patient comprising the steps:
providing an automated chest compression device comprising:
a backboard;
a support frame having two legs secured to the backboard, the two legs supporting a compression unit apposing the backboard;
a motor enclosed within the compression unit;
a piston having a distal end and a proximal end, the proximal end of the piston operably coupled to the motor and the motor configured to extend the piston distally and withdraw the piston proximally relative to the compression unit, the compression unit secured to the piston support frame with the piston apposing the backboard;
two resilient members, each resilient member having a first end and a second end, the first end of each resilient member operably secured to the piston, the second end of each resilient member operably secured to one of the two legs, such that extension of the piston causes each resilient member to form an arch suitable to apply lateral force to the patient's chest; and
orienting the patient on the backboard;
securing the support frame to the backboard with the piston apposing the patient's sternum; and
operating the chest compression device to cyclically compress the patient's chest with the piston and simultaneously apply lateral force to the patient's chest with the two resilient members.

8. A method of performing cardiopulmonary resuscitation on a patient comprising the steps:
providing a chest compression device having a piston for applying compression to the patient's sternum; and
providing two resilient members operably engaging the piston wherein the two resilient members are configured to apply lateral compression to the patient's thorax during chest compressions;
orienting the patient with the piston apposing the patient's sternum; and
operating the chest compression device to cyclically compress the patient's sternum with the piston and simultaneously apply lateral force to the patient's chest with the two resilient members.

* * * * *